United States Patent [19]

Kleschick et al.

[11] Patent Number: 4,874,421

[45] Date of Patent: Oct. 17, 1989

[54] HERBICIDAL METHOD WITH IMPROVED CROP TOLERANCE

[75] Inventors: William A. Kleschick, Martinez; Jacob Secor, Walnut Creek; Theodore W. Holmsen, Clayton, all of Calif.

[73] Assignee: The Dow Chemical Company, Midland, Mich.

[21] Appl. No.: 206,537

[22] Filed: Jun. 14, 1988

[51] Int. Cl.$^4$ ............................................. A01N 43/40
[52] U.S. Cl. ....................................................... 71/9 H
[58] Field of Search .......................................... 71/9 H

[56] References Cited

U.S. PATENT DOCUMENTS 4,628,099 12/1986 Johnston et al. .
4,678,509 7/1987 Johnston et al. .

OTHER PUBLICATIONS

J. Secor and C. Cseke, *Plant Physiology,* 86, 10–12 (1988).
F. C. Pallos and J. E. Casida, *Chemistry and Acton of Herbicide Antidotes,* pp. 151–164, Academic Press, 1978.

*Primary Examiner*—Catherine L. Mills
*Attorney, Agent, or Firm*—D. Wendell Osborne

[57] ABSTRACT

The selectivity of aryloxyphenoxypropanoate herbicides, such as methyl 2-(4-((3-chloro-5-(trifluoromethyl)-2-pyridinyl)oxy)phenoxy)propanoate, when used for the control of weeds in grassy crops, such as rice, can be improved by pre-treating the grassy crop seeds or plants with an amount of an aryloxyphenoxypropanoate herbicide sufficient to elevate the acetyl-coenzyme A carboxylase enzyme activity level, but insufficient to cause phytotoxicity.

9 Claims, No Drawings

HERBICIDAL METHOD WITH IMPROVED CROP TOLERANCE

BACKGROUND OF THE INVENTION

The practical use of herbicides in crops is dependent on the presence of good selectivity in phytotoxicity between the crop being treated and the undesirable vegetation to be controlled. This selectivity is mainly a function of the inate phytotoxic properties of the herbicide employed. Methods of improving the selective action of herbicides so that they can be safely used in crop situations where selectivity is marginal are highly desirable. Such methods would expand the utility of the herbicide and any yield loss due to the herbicide's action on the crop treated would be ameliorated.

Crop selectivity has previously been improved for certain herbicides by a variety of means, such as by the co-application of non-herbicidal chemical safeners specific to the herbicide and the crop, the selective placement of the herbicide, the timing of the herbicide application, the use of certain inert formulation ingredients with the herbicide, and the physical form of the formulation employed. Generally, however, these methods, while helpful, do not completely solve the problem in most situations and are not at all effective in others. New methods of improving the crop selectivity of herbicides are needed.

Many of the recently discovered herbicides that are especially effective on grassy weeds, including the aryloxyphenoxypropanoates, such as diclofop, haloxyfop, quizalofop, fluazifop, fenoxaprop, and fenthiaprop, and the cyclohexanediones, such as sethoxydim and tralkoxydim, are generally only marginally selective for use in many grassy crops, such as wheat, barley, rice, corn, and sorghum. These classes of herbicides are known to inhibit the enzyme acetyl-coenyzme A carboxylase (ACCase) in susceptible plants (*Plant Physiology,* 85, 10–12, 1988).

SUMMARY OF THE INVENTION

It has now been found that the selectivity to grass crops of herbicides which inhibit the enzyme ACCase, such as the aryloxyphenoxypropanoic acid and cyclohexanedione classes of herbicides, can be improved by pre-treating the crop with a sub-phytotoxic, but ACCase activity inducing amount of the same herbicide or of another herbicide which inhibits the enzyme ACCase, at some time prior to applying the amount required to control undesirable vegetation. In effect, the pre-treatment reduces the phytotoxicity of the herbicide to the crop when the herbicide is applied to control unwanted vegetation.

One embodiment of this invention is a method of controlling undesirable vegetation in rice crops which comprises contacting rice seeds or plants or the locus thereof with a sub-phytotoxic, acetyl-coenzyme A carboxylase activity level elevating amount of a pyridinyloxyphenoxypropanoate herbicide of the formula

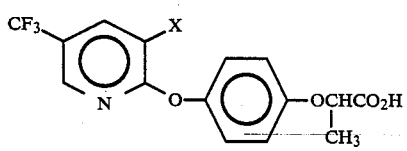

wherein X represents H, Cl, or F or an agriculturally acceptable salt, ester or amide thereof, and thereafter, within the period during which the acetyl-coenzyme A carboxylase activity level in the rice plants is elevated, contacting the rice plants or the locus thereof with an undesirable vegetation controlling amount of the same or another pyridinyloxyphenoxypropanoate herbicide of said formula.

It is often preferred to contact rice seeds in the sub-phytotoxic treatment step of the process. It is further preferred to employ the R optical isomer or a mixture of optical isomers enriched in the R isomer of the pyridinyloxyphenoxypropanoate compound. It is also preferred to employ a compound of the invention wherein X represents Cl and to employ the compounds in the form of a $C_1$–$C_4$ alkyl ester.

DETAILED DESCRIPTION OF THE INVENTION

The utility as selective herbicides of compounds that inhibit the enzyme acetyl-coenzyme A carboxylase (ACCase) for use in grassy crops is greatly improved when the grassy crop, its seeds, or the locus of the plants or its seed is pre-treated with an ACCase inhibiting herbicide in an amount sufficient to elevate the activity level of the enzyme in the crop, but insufficient to cause phytotoxicity. The crop or its locus is then treated with an unwanted vegetation controlling amount of the same compound or of another herbicide capable of inhibiting ACCase.

The process of the present invention is especially useful when the ACCase inhibiting compound employed is a pyridinyloxyphenoxypropanoate of the formula

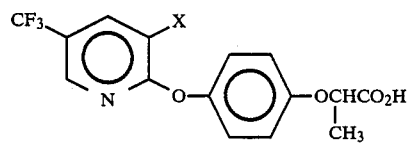

wherein X represents H, Cl, or F; or an agriculturally acceptable salt, ester or amide thereof. The preparation, herbicidal compositions, and herbicidal properties of these compounds are described in detail in U.S. Pat. Nos. 4,678,509 and 4,628,099, the appropriate teachings of which are hereby incorporated by reference. The compound, 2-(4-(3-chloro-5-(trifluormethyl)-2-pyridinyl)oxy)phenoxy)propanoic acid (X represents Cl) and its agriculturally acceptable salts, esters, and amides are preferred.

The compounds of the present invention have an assymmetric center and therefore optical isomers. The invention relates to both isomers and all mixtures of these isomers, but it is often preferred to employ the more active R isomer or mixtures of isomers enriched in the R isomer.

Agriculturally acceptable salts, esters and amides are those salts, esters and amides of the propanoic acid which have a cation, OR, $NH_2$, NHR, or $NR_2$ moiety that is not in itself herbicidal to crop plants nor significantly deleterious to the applicator, the environment, or the ultimate user of any crop being treated.

Suitable cations include, for example, those derived from alkali or alkaline earth metals and those derived from ammonia and amines. Preferred cations include sodium, potassium, magnesium, and aminium cations of the formula

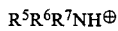

wherein $R^5$, $R^6$, and $R^7$ each, independently represents hydrogen or $C_1$-$C_{12}$ alkyl, $C_3$-$C_{12}$ cycloalkyl, or $C_3$-$C_{12}$ alkenyl, each of which is optionally substituted by one or more hydroxy, $C_1$-$C_8$ alkoxy, $C_1$-$C_8$ alkylthio or phenyl groups. Additionally, any two of $R^5$, $R^6$, and $R^7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

Suitable esters and amides include those wherein each R independently represents $C_1$-$C_8$ alkyl or $C_3$-$C_8$ alkenyl each substituted with up to 3 groups selected from $C_1$-$C_4$ alkoxy, F, Cl, Br, and phenyl. $C_1$-$C_4$ Alkyl esters are generally preferred and methyl and butyl esters are often specifically preferred.

The term alkyl as used herein includes straight chain, branched chain, and cyclic moieties. Thus, typical alkyl groups are methyl, ethyl, 1-methylethyl, 1,1-dimethylethyl, propyl, 2-methylpropyl, 1-methylpropyl, butyl and cyclopropyl.

The process is useful in some situations and to some extent for most grassy crops, including wheat, barley, oats, corn, rice and sorghum, and is especially useful when the grassy crop to be treated is rice. The treatment of rice with the compound, 2-(4-(3-chloro-5-(trifluoromethyl)-2-pyridinyl)oxy)phenoxy)propanoic acid or its agriculturally acceptable salts, esters, and amides under the conditions of the present invention is of particular interest.

The compounds of this invention can be employed directly in either step of the process, but they are usually employed in the form of a composition containing at least one agriculturally acceptable adjuvant or carrier as is taught in the art for their herbicidal applications.

The herbicide safening treatment of the grassy crop with a sub-phytotoxic amount of herbicide can be done by treating seeds before planting or by application to the planted seeds or seedlings or to the locus of the planting seeds or seedlings. It is often preferred to treat the seeds before planting since the amount of the chemical applied can be more carefully controlled in this type of treatment. Any of the methods of treating seeds known to those in the art can be employed. Planted seeds or seedlings or their locus can be treated using any of the herbicide application methods known to those in the art. The treatments can be pre- or postemergence, and can be incorporated or allowed to remain on the soil surface. Directed sprays and banded treatments are preferred so that as a practical matter only the crop seeds or seedlings (not the undesirable vegetation) are treated.

The amount of the compound of the invention applied in the initial, safening treatment is an amount sufficient to increase the activity level of the enzyme ACCase in the crop plant, but insufficient to cause plant injury. The increase observed in the activity level of this enzyme in the crop plant is a result of the plant's natural response to small amounts of the enzyme inhibiting compound. The exact amount to be used depends upon the crop species to be protected, the type of soil, the stage of growth of the plants (or seeds), the application parameters of dilution and spray drop size, the particle size of solid components, the environmental conditions at the time of the application, the specific compound employed, the specific adjuvants and carriers employed, and the like, as well as the amount of chemical applied. In general, for rice, amounts of about 0.5 mg to about 100 mg of chemical per kilogram of seed are suitable for seed treatments and amounts of about 4 to about 30 mg/kg are preferred. For directed spray foliar treatments, about 1 to about 30 grams per hectare are suitable and about 3 to about 15 g/ha are preferred, while for banded soil treatments, about 20 to about 400 grams per hectare within the treated band are suitable and about 50 to about 200 g/ha are preferred. The amount employed for soil treatment is especially dependent on soil type, soils having a higher organic matter content requiring larger amounts.

The herbicidal application of the compounds of the present invention (second step of the invention) can also be done by any of the application methods known to those in the art. Either pre- or postemergence methods can be used and both overall application and selective application methods, as with directed sprays or banding, are suitable. It is generally preferred to use postemergence application methods.

The herbicidal application must be made during the time that the ACCase activity in the crop plant is elevated as a result of the previous sub-lethal application. Generally, this can be any time greater than about 12 hours after the sub-phytotoxic treatment of growing plants or their locus or of planting treated seeds. It is preferred to make the application after about 1 day and before about 60 days of these same events and more preferred between about 2 days and about 30 days.

The amount of compound of the present invention to be applied in the herbicidal treatment step of the process is an amount sufficient to kill or control the unwanted grassy vegetation present or expected to emerge within the current growing season. The exact amount employed depends upon the plant species to be controlled, the stage of growth of the plant, the application parameters of dilution and spray drop size, the particle size of solid components, the environmental conditions at the time of the test, the specific compound employed, the specific adjuvants and carriers employed, the soil type, and the like. An appropriate rate for each crop, compound and circumstance can be determined by simple range finding tests using the teachings herein in conjunction with the disclosures of U.S. Pat. Nos. 4,628,099 and 4,678,509, the appropriate teachings of which are hereby incorporated by reference, and the known art surrounding these herbicides. Generally, application rates in the range of about 0.01 kg/ha to about 1 kg/ha are employed. Rates in the range of about 0.02 to about 0.5 kg/ha are usually preferred when the crop is rice. Preemergence treatments usually require considerably more chemical that postemergence treatments.

An herbicidally effective amount or an amount sufficient to control unwanted vegetation is an amount of active ingredient which causes an adversely modifying effect and includes deviations from natural development, killing, regulation, dessication, retardation, and the like. The term unwanted vegetation includes germinant seeds, emerging seedlings and established vegetation. A sub-phytotoxic amount is an amount sufficiently small that it causes no overt symptoms of damage.

The following examples are presented to illustrate the invention. They should not be construed as limiting the claims.

plants off at the level of the lip of the pot and dried in a forced air oven at 80° C. to constant weight.

The results obtained, which demonstrate the increase in ACCase as well as the protection afforded by the pre-treatment, are given in the following table.

| Pre-treatment Rate, ppm | ACCase Activity, nmol/min/mg (before desalting) | ACCase Activity, Percent of the Control | ACCase Activity, nmol/min/mg (after desalting) | ACCase Activity, Percent of the Control | Weight per Pot, g Pre-Treatment Only | Dry Weight per Pot, g Pre- and Post Treatment |
| --- | --- | --- | --- | --- | --- | --- |
| 0.00 | 2.31 | (100) | 1.41 | (100) | 1.82 | 1.46 |
| 0.05 | 2.60 | 113 | 1.69 | 120 | 1.83 | 1.49 |
| 0.50 | 2.92 | 126 | 2.62 | 186 | 2.07 | 1.80 |

EXAMPLES

EXAMPLE 1

Increase in ACCase Activity in Rice Plants Pre-treated with Methyl 2-(4-((3-Chloro-5-(trifluoromethyl)-2-pyridinyl)oxy)-phenoxy)propanoate and Its Protective Effect About 25-30 rice seeds were planted in sandy loam soil in each of a number of 3 inch diameter by 3 inch deep pots. Twenty pots were treated by pouring in 50 ml of an aqueous emulsion containing 0.05 or 0.50 ppm of methyl 2-(4-((3-chloro-5-(trifluoromethyl)-2-pyridinyl)oxy)phenoxy)propanoate, prepared by dilution of a commercial emulsifiable concentrate formulation. Another set of ten control pots were prepared and treated analogously. The pots were placed in a greenhouse under conditions conducive to germination and growth. After 13 days pots were divided into two groups, one with 4 treatment (2 of each dosage) and 2 untreated control pots and one with 16 treatment (8 of each dosage) and 8 untreated control pots.

The plant material from each pot of the first group was separately removed by cutting off the plants at the level of the lip of the pot, weighed, and ground with a mortar and pestle. An aqueous buffer solution containing 10% (v/v) glycerol and 100 mM Tricine-KOH (pH 8.3), 10 mM beta-mercaptoethanol, 1 mM disodium ethylenediaminetetraacetic acid, and 1 mM phenylmethyl sulfonyl fluoride was prepared and 12 ml aliquots added to each sample. The mixtures were then individually filtered through 4 layers of cheese cloth and 2 layers of Miracloth and the filtrate was centrifuged for 20 min at 30,000×gravity. A portion of each supernatant solution obtained was then assayed for ACCase activity using the method described in *Plant Physiology*, 86, 10-12 (1988). A second portion of each of the supernatant liquids was passed through a Sephadex G-25 desalting column and then assayed for ACCase.

The second group of plants was divided into two equal sets, each containing four replications of each pre-treatment (0.05 and 0.50 ppm) and four untreated controls. One of the sets was sprayed with an emulsion containing methyl 2-(4-((3-chloro-5-(trifluoromethyl)-2-pyridinyl)oxy)phenoxy)propanoate (prepared by dilution of a commercial emulsifiable concentrate formulation) at the rate of 100 g/ha using a track sprayer. The other set was not given a herbicidal treatment. The plants were placed in a greenhouse under conditions conducive to growth. After 7 days the plant material from each pot was separately removed by cutting the

EXAMPLE 2

Increase in ACCase Activity in Rice Plants Pre-treated with Methyl 2-(4-((3-Chloro-5-(trifluoromethyl)-2-pyridinyl)oxy)-phenoxy)propanoate and Its Protective Effect The procedure described in Example 1 was followed except that the pre-treatment emulsion contained 0.125 ppm of the herbicide and the herbicidal treatment was at the rate of 50 g per hectare and twice as many replications were employed. Thus, there were four replications of each data point in the ACCase activity determination and eight replications of each data point in the plant weight determination. In addition, the plants were allowed to grow for 17 days after the herbicidal application before weight measurements were taken. Further, only the ACCase activity measurement before desalination was obtained and only 10 ml aliquots of the buffer solution were employed.

The ACCase activity levels in the control and pre-treated plants were found to be 8.6 and 11.2 nmol/min/mg, respectively, which represents an increase of 30 percent in the pre-treatment plants. The dry weights of the control plants (no pre-treatment or herbicidal treatment) was found to average 2.53 g/pot while the dry weights of the plants given only the pre-treatment averaged 2.55 g/pot and the dry weights of the plants given both the pre-treatment and the herbicidal treatment averaged 2.52 g/pot. In contrast, the plants given only the herbicidal treatment (no pre-treatment) averaged 2.00 g/pot. The difference is statistically significant at the 96 percent confidence level.

What is claimed is:

1. A method of selectively controlling undesirable vegetation in rice crops which comprises contacting rice seeds or plants with a crop-protecting sub-phytotoxic, acetyl-coenzyme A carboxylase and thereafter, within the period during which the acetyl-coenzyme A carboxylase activity level in the rice plants is elevated, contacting the rice plants and the locus thereof postemergently with an undesirable vegetation controlling amount of the same pyridinyloxyphenoxypropanoate herbicide.

2. A method according to claim 1 wherein the sub-phytotoxic contact is with rice seeds.

3. A method according to claim 1 wherein the undesirable vegetation controlling contact is a post-emergence application.

4. A method according to claim 1 wherein the R isomer of the herbicide or a mixture of isomers enriched in the R isomer is employed.

5. A method according to claim 1 wherein X represents Cl.

6. A method according to claim 1 wherein the herbicide is in the form of a $C_1$–$C_4$ alkyl ester.

7. A method according to claim 6 wherein the ester is methyl or butyl.

8. A method of selectively controlling undesirable vegetation in rice crops which comprises contacting rice seeds with a crop protecting, sub-phytotoxic, acetyl-coenzyme A carboxylase activity level elevating amount of a pyridinyloxyphenoxypropanoate herbicide of the formula

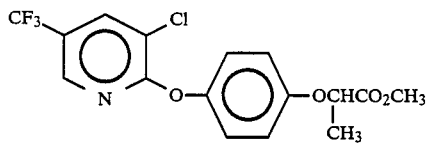

activity level elevating amount of a pyridinyloxyphenoxypropanoate herbicide of the formula

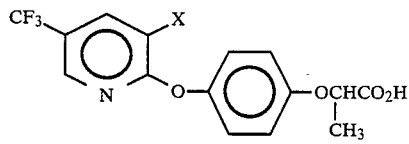

wherein X represents H, Cl, or F or an agriculturally acceptable salt, ester or amide thereof, and thereafter, within the period during which the acetyl-coenzyme A carboxylase activity level in the rice plants is elevated, contacting the rice plants and the locus thereof with an undesirable vegetation controlling amount of the same or another pyridinyloxyphenoxypropanoate herbicide of said formula.

9. A method according to claim 8 wherein the R isomer of the herbicide or a mixture of isomers enriched in the R isomer is employed.

* * * * *

UNITED STATES PATENT AND TRADEMARK OFFICE
CERTIFICATE OF CORRECTION

PATENT NO. : 4,874,421
DATED : October 17, 1989
INVENTOR(S) : William A. Kleschick et al.

It is certified that error appears in the above-identified patent and that said Letters Patent is hereby corrected as shown below:

Col. 6, line 54, after "carboxylase", insert
-- activity level elevating amount of a pyridinyloxyphenoxy-propanoate herbicide of the formula

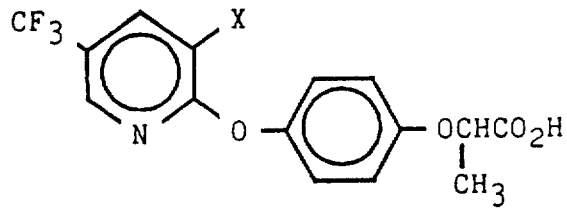

wherein X represents H, Cl, or F or an agriculturally acceptable salt, ester or amide thereof, --;

Col. 6, line 58, delete "postemergently";

Col. 6, line 59, after "same" insert
-- or another --;

UNITED STATES PATENT AND TRADEMARK OFFICE
CERTIFICATE OF CORRECTION

PATENT NO. : 4,874,421
DATED : October 17, 1989
INVENTOR(S) : William A. Kleschick et al.

It is certified that error appears in the above-identified patent and that said Letters Patent is hereby corrected as shown below:

Col. 6, line 60, delete "herbicide." and insert -- herbicide of said formula. --;

Col. 8, line 1, delete "activity level elevating amount of a pyridinyloxy-phenoxypropanoate herbicide of the formula

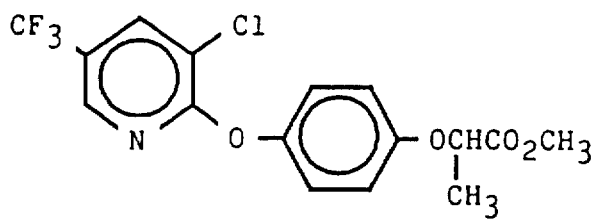

wherein X represents H, Cl, or F or an agriculturally acceptable salt, ester or amide thereof,";

UNITED STATES PATENT AND TRADEMARK OFFICE
CERTIFICATE OF CORRECTION

PATENT NO. : 4,874,421

DATED : October 17, 1989

INVENTOR(S) : William A. Kleschick et al.

It is certified that error appears in the above-identified patent and that said Letters Patent is hereby corrected as shown below:

Col. 8, line 15, after "thereof" insert -- postemergently --;

Col. 8, line 17, after "herbicide" delete "of said formula".

Signed and Sealed this

Fifth Day of May, 1992

Attest:

DOUGLAS B. COMER

Attesting Officer

Acting Commissioner of Patents and Trademarks